(12) United States Patent
Lorant

(10) Patent No.: US 6,335,025 B1
(45) Date of Patent: Jan. 1, 2002

(54) WATER-IN-OIL EMULSION AND USE THEREOF IN A COSMETIC COMPOSITION

(75) Inventor: Raluca Lorant, Thiais (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 09/692,361

(22) Filed: Oct. 20, 2000

(30) Foreign Application Priority Data

Oct. 21, 1999 (FR) .................................... 99 13146

(51) Int. Cl.$^7$ ................................ A61K 7/00; A61K 7/42; A61K 7/48
(52) U.S. Cl. .................... 424/401; 424/59; 424/70.01; 424/70.12; 424/70.13; 424/70.19; 424/78.03
(58) Field of Search .................... 424/401, 59, 70.01, 424/70.13, 70.19, 70.12, 78.03

(56) References Cited

U.S. PATENT DOCUMENTS

| | | | |
|---|---|---|---|
| 6,074,653 A | * | 7/1998 | Wilcox et al. ................ 424/401 |
| 5,888,482 A | * | 3/1999 | Amalric et al. ............... 424/59 |
| 6,159,486 A | * | 5/1999 | Terren et al. ................ 424/401 |

FOREIGN PATENT DOCUMENTS

| | | |
|---|---|---|
| EP | 0 531 943 A1 | 3/1993 |
| FR | 2 669 345 | 5/1992 |
| FR | WO 0056438 * | 3/1999 |

* cited by examiner

*Primary Examiner*—Diana Dudash
*Assistant Examiner*—Mina Haghighatian
(74) *Attorney, Agent, or Firm*—Oblon, Spivak, McClelland, Maier & Neustadt, P.C.

(57) ABSTRACT

The present invention relates to a water-in-oil emulsion, in particular a cosmetic emulsion, comprising (i) an alkylpolyglycoside having an HLB of less than 7, and (ii) at least one volatile oil. The alkyl chain of the alkylpolyglycoside preferably contains from 14 to 24 carbon atoms and can be in particular an unsaturated linear chain and/or a branched chain, and more particularly an oleyl or isostearyl chain. The volatile oil can be chosen in particular from branched-chain hydrocarbon-based oils and volatile silicone oils, and mixtures thereof. The emulsion obtained is stable and feels fresh when applied. It can be used in particular for caring for the skin, the nails and the hair, for removing make-up from and/or for cleansing the skin, and/or for making up the skin.

26 Claims, No Drawings

WATER-IN-OIL EMULSION AND USE THEREOF IN A COSMETIC COMPOSITION

BACKGROUND OF THE INVENTION

1. Field of the Invention

The present invention relates to a water-in-oil emulsion containing an alkylpolyglycoside having an HLB of less than 7 and at least one volatile oil, and to its uses, in particular, in cosmetics. The present invention may be used, in particular, for caring for the skin, the lips, the nails and the hair, for removing make-up from and/or for cleansing the skin, and/or for making up the skin and/or the lips. Moreover, the present invention may also be used for treating dry skin and/or dry lips and/or sensitive skin.

2. Description of the Background

It is common practice in cosmetics to use creams consisting of a water-in-oil (W/O) emulsion containing an aqueous phase dispersed in an oily phase. These emulsions contain a continuous oily phase, whereby it is possible to form a lipid film at the surface of the skin which prevents transepidermal water loss and protects the skin against external attack. These emulsions are particularly suitable for caring for and repairing dry and dehydrated skin, to which they provide comfort and protection by means of the lipid barrier which they form on the skin.

However, despite their great efficacy, W/O emulsions only constitute a small proportion of the pharmaceutical forms used in cosmetics, since they pose two major problems. Firstly, these emulsions have the drawback of generally lacking in cosmetic pleasantness, i.e. they are greasy, heavy, sticky and lack a fresh sensation on account of the oily outer phase. They are generally difficult to apply to the skin, penetrate with difficulty and leave a shiny and often sticky remnant film on the skin.

Moreover, W/O emulsions have stability problems and it is often necessary, in order to achieve stabilization, to use a large amount of emulsifiers and/or to introduce a certain amount of consistency factors, such as waxes. However, these ingredients exacerbate the cosmetic defects, i.e. stickiness and greasiness, of the W/O emulsions, the result of which is the production of compositions that are often compact and heavy. Furthermore, if the amount of emulsifier in these emulsions is greatly increased in an attempt to overcome their instability, the emulsions obtained are an irritant to certain types of skin, in particular, sensitive skin.

Although alkylpolyglycosides (APGs) are known as emulsifiers, conventionally APGs so used generally have an HLB (hydrophilic-lipophilic balance) of greater than 8, and are generally used to prepare O/W emulsions. In order to prepare W/O emulsions, it is generally necessary to combine them with another APG or with another surfactant. Thus, for example, U.S. Pat. No. 5,639,797 describes a W/O emulsion containing a hydrophilic APG, such as decylglucoside, i.e. having an HLB of greater than 8, which must be combined with a W/O surfactant in order to obtain the desired emulsion. Moreover, it is often necessary to use a large total amount of surfactants in order to obtain a stable W/O emulsion.

Thus, a need exists for a stable water-in-oil emulsion which avoids the above drawbacks.

SUMMARY OF THE INVENTION

Accordingly, it is an object of the present invention to provide a water-in-oil emulsion which has good cosmetic properties, such as a simultaneously light, fresh and rich feel, and good stability by using a certain alkylpolyglycoside as emulsifier, and volatile oils.

It is also an object of the present invention to provide a cosmetic composition based upon the water-in-oil emulsion.

In particular, the present invention provides a water-in-oil emulsion, containing an aqueous phase dispersed in an oily phase, containing (i) an alkylpolyglucoside having an HLB of less than 7, and (ii) at least one volatile oil.

DETAILED DESCRIPTION OF THE PREFERRED EMBODIMENTS

The present invention provides a water-in-oil emulsion (w/o) containing an aqueous phase dispersed in an oily phase, which contains (i) an alkylpolyglycoside having an HLB of less than 7, and (ii) at least one volatile oil.

The emulsions of the present invention spread easily and are absorbed quickly and completely into the skin. Along with a rich and nourishing feel, they provide a surprising sensation of freshness. After the product of the present invention has been applied, the skin remains soft and matt. Moreover, the emulsions of the present invention can have a creamy texture or can be fluid while at the same time having good stability. The fluid emulsions generally have a viscosity ranging from about 0.2 Pa.s to 3 Pa.s (2 to 30 poises) and preferably from about 0.6 Pa.s to 2 Pa.s (6 to 20 poises), this viscosity being measured at about 25° C. using a "Mettler Rhéomat" viscometer equipped with a No. 2 spindle (for viscosities of less than 7 poises) or a No. 3 spindle (for viscosities of greater than 7 poises).

The alkylpolyglycosides used according to the present invention have an HLB of less than 7, and preferably of less than or equal to 5. In contrast, the alkylpolyglycosides conventionally used in cosmetic compositions have generally an HLB of more than 10 and are either detergents (HLB generally more than 13) or emulsifying agents for oil-in-water emulsions (HLB about from 10 to 17). HLB may be calculated particularly by either Davies's Method or Griffin's Method.

The alkylpolyglycosides of the present invention are represented more particularly by the formula (I) below:

$$R\text{—}O\text{—}(G)_x \qquad (I)$$

in which R represents a branched and/or unsaturated alkyl radical containing from about 14 to 24 carbon atoms, G represents a reduced sugar containing about 5 or 6 carbon atoms and x denotes a value ranging from 1 to 10 and preferably from 1 to 4.

G, in particular, denotes glucose, fructose or galactose.

The unsaturated alkyl radical (alkylene radical) can contain one or more ethylenic unsaturations, and in particular one or two ethylenic unsaturations.

The alkylpolyglycosides that are preferred according to the present invention are compounds of formula (I) in which R more particularly represents an oleyl radical (unsaturated C18 radical) or an isostearyl radical (saturated C18 radical), G denotes glucose and x is a value ranging from 1 to 2.

The alkylpolyglycoside used in the emulsion of the present invention is preferably isostearylglucoside or oleylglucoside, or mixtures thereof.

According to one particular embodiment of the present invention, the emulsion can contain, besides the alkylpolyglycoside indicated above, a co-emulsifier. The co-emulsifier can be chosen advantageously from fatty alcohols and, in particular, from those containing the same fatty chain as that of the alkylpolyglycoside, i.e. containing from about 14 to 24 carbon atoms and having a branched and/or unsaturated chain, and, for example, isostearyl alcohol when the alkylpolyglycoside is isostearylglucoside, and oleyl alcohol when the alkylpolyglycoside is oleylglucoside.

According to one preferred embodiment of the invention, the mixture of alkylpolyglycoside as defined above with the corresponding fatty alcohol is used in the emulsion according to the present invention in the form of a self-emulsifying composition, as described, for example, in WO-A-92/06778.

The emulsion according to the present invention can contain an amount of alkylpolyglycoside(s) ranging, for example, from about 0.1% to 10%, and preferably from about 0.2% to 5% by weight of active material relative to the total weight of the composition. When it is mixed with the corresponding fatty alcohol, the latter is present in an amount generally ranging from about 60% to 90% by weight and preferably from about 70% to 87% by weight relative to the weight of the mixture of alkylpolyglycoside and fatty alcohol.

The oily phase of the emulsion according to the present invention contains at least one volatile oil. In the present description, the term "volatile oil" means any oil which can evaporate on contact with the skin and/or which has a low flash point, i.e. a flash point of less than about 100° C., and in particular a flash point of between 30° C. and 85° C., i.e. an oil whose flash point is high enough to allow these oils to be used in formulation, and low enough to obtain the desired evanescence on the skin.

Volatile oils which may be mentioned, for example, are branched-chain hydrocarbon- based oils, or linear or cyclic volatile silicone oils, such as cyclotetradimethylsiloxane (flash point 55° C.), cyclopentadimethylsiloxane (flash point about 77° C.), cyclohexadimethylsiloxane (flash point 76° C.) or methylhexyldimethylsiloxane (flash point 79° C.). These oils can be used alone or as a mixture.

The branched-chain hydrocarbon-based oils which can be used as volatile oils in the emulsion of the invention preferably contain from about 6 to 20 and better still from about 6 to 18 carbon atoms and are, for example, isohexadecane, isododecane, isoparaffins, or mixtures thereof.

The oily phase can also contain any fatty substance conventionally used in cosmetics. The fatty substances may be, for example, oils other than those mentioned above, fatty acids, fatty alcohols and waxes.

Among the oils which can be used in the emulsion of the present invention, mention may be made, for example, of plant oils such as apricot kernel oil and soybean oil; mineral oils such as liquid petroleum jelly; synthetic oils; nonvolatile silicone oils and fluoro oils, such as fluorosilicone oils. Other fatty substances which may be mentioned, for example, are beeswax and petroleum jelly.

When the emulsion is used as a make-up-removing product for the skin and/or the eyes, it more particularly contains make-up-removing oils and especially those chosen from esters of a fatty acid containing at least about 12 carbon atoms. These esters are preferably obtained from a straight-chain or branched-chain alcohol containing from 1 to about 17 carbon atoms and from a straight-chain or branched-chain fatty acid containing at least about 12 carbon atoms and preferably from about 14 to 22 carbon atoms. They are preferably mono- or diesters. The make-up-removing oils can be chosen in particular from the group comprising 2-ethylhexyl palmitate (or octyl palmitate), 2-ethylhexyl myristate (or octyl myristate), isopropyl palmitate, isopropyl myristate, diisopropyl adipate, diocryl adipate, 2-ethylhexyl hexanoate, ethyl laurate, methyl myristate, octyldodecyl octanoate, isodecyl neopentanoate, ethyl myristate, myristyl propionate, 2-ethylhexyl 2-ethylhexanoate, 2-ethylhexyl octanoate, 2-ethylhexyl caprate/caprylate, methyl palmitate, butyl myristate, isobutyl myristate, ethyl palmitate, isohexyl laurace, hexyl laurate and isopropyl isostearate, and mixtures thereof.

The amount of oily phase in the emulsion of the invention can range, for example, from about 5% to 50% and preferably from about 10% to 40% by weight relative to the total weight of the emulsion. The volatile oil(s) can represent all or a part of this oily phase, and it(they) preferably represent(s) from about 30% to 95% by weight relative to the total weight of the oily phase.

The aqueous phase of the emulsion can represent, for example, from about 50% to 95% and preferably from about 60% to 90% by weight relative to the total weight of the emulsion.

The emulsion of the invention can in particular constitute a cosmetic or dermatological composition intended for application to the skin, the hair and/or mucous membranes. In this case, it advantageously contains a physiologically acceptable medium, i.e. a medium which is compatible with the skin, mucous membranes (lips) and/or the hair.

In a known manner, the emulsion of the invention can also contain adjuvants that are common in cosmetics, such as active agents, preserving agents, antioxidants, complexing agents, solvents, fragrances, fillers, screening agents, bactericides, odour absorbers, dyestuffs (soluble pigments or dyes) and lipid vesicles. The amounts of these various adjuvants are those conventionally used in the field under consideration, and, for example, from about 0.01% to 20% relative to the total weight of the composition. Depending on their nature, these adjuvants can be introduced into the oily phase, into the aqueous phase and/or into the lipid vesicles.

According to one particular embodiment of the present invention, the emulsion comprises at least one filler whose incorporation further improves the stability of the emulsion as well as its matt effect on the skin. As fillers which can be used in the emulsion of the invention, mention may be made, for example, besides pigments, of polyamide particles and in particular of those sold under the name Orgasol by the company Atochem; polyethylene powders; microspheres made from acrylic copolymers, such as those made from ethylene glycol dimethacrylate/lauryl methacrylate copolymer, which are sold by the company Dow Coming under the name Polytrap; expanded powders such as hollow microspheres and in particular the microspheres sold under the name Expancel by the company Kemanord Plast or under the name Micropearl F 80 ED by the company Matsumoto; powders of naturally-occurring organic materials such as crosslinked or non-crosslinked corn, wheat or rice starches, such as the starch powders crosslinked with octenylsuccinic anhydride which are sold under the name Dry-Flo by the company National Starch; silicone resin microbeads such as those sold under the name Tospearl by the company Toshiba Silicone; and mixtures thereof.

The fillers preferably used are Expancel microspheres, which are particles of expanded vinylidene chloride, acrylonitrile and methacrylate terpolymer, and in particular those sold under the references 551 having a particle size ranging from about 10 μm to 100 μm (551 DE 12, 551 DE 20, 551 DE 50 and 551 DE 80) and those sold under the reference EL 23 (particle size of about 18 μm).

In the case of make-up products and in particular foundations, the filler can consist of pigments.

When the emulsion of the invention contains fillers, the amount of filler(s) can range, for example, from about 0.01% to 15% and preferably from about 0.1% to 5% by weight relative to the total weight of the emulsion.

The emulsion according to the present invention can also contain one or more salts, and in particular a magnesium salt such as magnesium sulfate. The amount of salt(s) can range, for example, from about 0.1% to 5% and preferably from about 0.5% to 1% by weight relative to the total weight of the emulsion.

The emulsion according to the present invention finds its application in a large number of treatments, in particular cosmetic treatments for the skin, the lips and the hair, including the scalp, especially for treating, protecting, caring for, removing make-up from and cleansing the skin, the lips and/or the hair, and/or for making up the skin and/or the lips. It may also be intended for treating dry skin and/or dry lips.

The emulsion according to the invention can be used, for example, as a care product, a make-up-removing product and/or a cleansing product for the face in the form of creams or milks or as make-up products (for skin and lips) and, for example, foundations, by incorporating fillers or dyes.

Thus, the present invention may be used for treating, protecting, caring for, removing make-up from and/or cleansing the skin, the lips and/or the hair, and/or for making up the skin and/or the lips.

The present invention may also be used in a cosmetic treatment process for the skin, including the scalp, the hair and/or the lips, wherein an emulsion as defined above is applied to the skin, the hair and/or the lips.

The present convention may also be used for the manufacture of a composition intended for caring for dry skin and/or dry lips and/or sensitive skin.

Having described the present invention, reference will now be made to certain examples which are provided solely for purposes of illustration and are not intended to be limitative. The amounts therein are given as percentages by weight, except where otherwise mentioned.

EXAMPLE 1

Moisturizing Fluid for all Skin Types

| Oily phase: | |
|---|---|
| Isostearylglucoside/isostearyl alcohol (15/85) (i.e. 0.75% alkylpolyglycoside active material) | 5% |
| Isohexadecane | 15% |
| Cyclohexamethicone | 10% |
| Filler: | |
| Expancel 551 | 1% |
| Aqueous phase: | |
| Glycerol | 5% |
| Magnesium sulphate | 0.5% |
| Preserving agents | 0.4% |
| Water | qs 100% |

Procedure: The filler is dispersed in the oily phase and an emulsion is then formed by dispersing the aqueous phase in the mixture obtained, with vigorous stirring.

A fluid is thus obtained which feels very soft when applied, has a simultaneous sensation of richness and freshness, is non-greasy and penetrates quickly into the skin, which it leaves soft, matt and supple.

EXAMPLE 2

Nourishing Care Cream for Dry and Sensitive Skin

| Oily phase: | |
|---|---|
| Isostearylglucoside/isostearyl alcohol (15/85) (i.e. 0.45% alkylpolyglycoside active material) | 3% |
| Apricot kernel oil | 8% |
| Cyclohexamethicone | 8% |
| Petroleum jelly | 1% |
| Beeswax | 1% |
| Aqueous phase: | |
| Glycerol | 5% |
| Magnesium sulfate | 0.5% |
| Preserving agents | 0.4% |
| Water | qs 100% |

Procedure: The oily and aqueous phases are heated separately to 75° C. and an emulsion is then formed by dispersing the aqueous phase in the oily phase, with vigorous stirring.

An unctuous cream is thus obtained which feels soft and rich when applied. It penetrates easily, immediately giving a soothing nourishing effect.

EXAMPLE 3

Make-up-removing Milk for Dry Skin

| Oily phase: | |
|---|---|
| Oleylglucoside/oleyl alcohol (16.5/83.5) (i.e. 0.495% alkylpolyglycoside active material) | 3% |
| Liquid petroleum jelly | 10% |

-continued

| | |
|---|---|
| Cyclopentamethicone | 10% |
| Octyl palpitate | 10% |
| Filler: | |
| Expancel 551 | 0.5% |
| Aqueous phase: | |
| Glycerol | 5% |
| Magnesium sulfate | 0.5% |
| Preserving agents | 0.4% |
| Water | qs 100% |

Procedure: The filler is dispersed in the oily phase and an emulsion is then formed by dispersing the aqueous phase in the mixture obtained, with vigorous stirring.

A milk is thus obtained which is particularly pleasant to use and which has very good make-up-removing properties. This milk, which feels very unctuous when applied, gently removes make-up and impurities without aggravating or irritating the skin.

After removal, the skin is soft, matt and fresh.

EXAMPLE 4

Foundation for Dry Skin

| Oily phase: | |
|---|---|
| Isostearylglucoside/isostearyl alcohol (15/85) (i.e. 0.45% alkylpolyglycoside active material) | 3% |
| Soybean oil | 2% |
| Cyclohexamethicone | 18% |
| Filler: | |
| Brown, red and yellow pigments | 5% |
| Aqueous phase: | |
| Glycerol | 5% |
| Magnesium sulfate | 0.5% |
| Preserving agents | 0.4% |
| Water | qs 100% |

Procedure: The fillers are dispersed in the oily phase and an emulsion is then formed by dispersing the aqueous phase in the mixture obtained, with vigorous stirring.

A foundation of soft texture is thus obtained, which feels very soft when applied, and is easy to spread. It gives a homogeneous, matt, natural make-up result.

The emulsion and compositions containing the same of the present invention may be used as described above with all mammals, however, they are particularly advantageous when used for and by humans. The emulsion and composition containing the same may be applied manually to the hair, skin and/or lips or may be directly applied thereto from a container or other dispenser.

Having described the present invention, it will be apparent to one of ordinary skill in the art that many changes and modifications may be made to the above-described embodiments without departing from the spirit and the scope of the present invention.

What is claimed is:

1. A water-in-oil emulsion, comprising an aqueous phase dispersed in an oily phase, comprising (i) an alkylpolyglycoside having an HLB of less than 7, and (ii) at least one volatile oil.

2. The emulsion of claim 1, wherein the alkylpolyglycoside has the formula (I):

$$R\text{—}O\text{—}(G)_x \qquad (I)$$

in which R is a branched or unsaturated alkyl radical or both containing from about 14 to 24 carbon atoms, G is a reduced sugar containing about 5 or 6 carbon atoms, and x has a value ranging from 1 to about 10.

3. The emulsion of claim 2, wherein G is glucose, fructose or galactose.

4. The emulsion of claim 2, wherein in formula (I), R is an oleyl or isostearyl radical, G is glucose and x has a value ranging from 1 to 2.

5. The emulsion of claim 1, wherein the alkylpolyglycoside is selected from the group comprising isostearylglucoside, oleylglucoside, and mixtures thereof.

6. The emulsion of claim 1, wherein the amount of alkylpolyglycoside(s) ranges from about 0.1% to 10% by weight of active material relative to the total weight of the emulsion.

7. The emulsion of claim 1, wherein the alkylpolyglycoside is present as a mixture with a fatty alcohol containing from about 14 to 24 carbon atoms and having a branched or unsaturated chain or both.

8. The emulsion of claim 7, wherein the amount of fatty alcohol ranges from about 60% to 90% by weight relative to the weight of the mixture of alkylpolyglycoside and fatty alcohol.

9. The emulsion of claim 1, wherein the volatile oil is selected from the group consisting of branched-chain hydrocarbon-based oils and volatile silicone oils, and mixtures thereof.

10. The emulsion of claim 9, wherein the volatile oil is selected from the group consisting of isohexadecane, isododecane, isoparaffins and cyclomethicones, and mixtures thereof.

11. The emulsion of claim 1, wherein the amount of oily phase ranges from about 5% to 50% by weight relative to the total weight of the emulsion.

12. The emulsion of claim 1, which comprises at least one filler.

13. The emulsion of claim 9, wherein the volatile oil is selected from the group consisting of cyclotetradimethylsiloxane, cyclopentadimethylsiloxane, cyclohexadimethylsiloxane, and methylhexyldimethylsiloxane.

14. The emulsion of claim 1, wherein the oily phase further contains one or more plant oils or waxes, mineral oils, synthetic oils, non-volatile silicone oils, fluoro oils, beeswax, or petroleum jelly or any combination thereof.

15. The emulsion of claim 1, wherein the oily phase further contains esters of a fatty acid containing at least twelve carbon atoms.

16. The emulsion of claim 12, wherein said filler comprises pigments, polyamide particles, polyethylene powders, microspheres made from acrylic copolymers, powders of naturally-occurring materials, or silicone resin microbeads.

17. The emulsion of claim 1, further comprising one or more salts.

18. The emulsion of claim 12, wherein the filler ranges from about 0.01% to 15% by weight relative to the total weight of the emulsion.

19. A cosmetic composition, comprising at least the emulsion of claim 1.

20. A method for treating, protecting, caring for, removing make-up from, or cleansing skin, lips or hair, or for making up the skin or the lips, or any combination thereof, of a human, which comprises administering an effective amount of the water-in-oil emulsion of claim 1, to said skin, lips or hair or any combination thereof to said human.

21. The method of claim 20, which comprises treating the skin.

22. The method of claim 20, which comprises removing make-up from the skin or lips.

23. The method of claim 20, which comprises making-up the skin or lips.

24. The method of claim 20, which comprises treating the hair.

25. The method of claim 21, wherein the skin is dry skin.

26. The method of claim 23, wherein the lips are dry lips.

* * * * *